United States Patent [19]

Girard et al.

[11] Patent Number: 5,248,689
[45] Date of Patent: Sep. 28, 1993

[54] SUBSTITUTED N-(IMIDAZOLYL)ALKYL ALANINE DERIVATIVES

[75] Inventors: Gerald R. Girard, Bensalem; David T. Hill, North Wales; Joseph Weinstock, Phoenixville, all of Pa.

[73] Assignee: SmithKline Beecham Corporation, Philadelphia, Pa.

[21] Appl. No.: 590,206

[22] Filed: Sep. 28, 1990

Related U.S. Application Data

[63] Continuation-in-part of Ser. No. 432,111, Nov. 6, 1989, abandoned.

[51] Int. Cl.$^5$ .................. A61K 31/415; C07D 257/02; C07D 233/30; C07D 233/42
[52] U.S. Cl. ..................................... 514/397; 514/269; 514/341; 514/365; 514/374; 514/376; 514/381; 514/383; 514/384; 514/398; 514/400; 544/333; 546/278; 548/112; 548/171; 548/252; 548/264.4; 548/315.1; 548/316.4; 548/321.1; 548/322.5; 548/323.5; 548/324.1; 548/325.5; 548/328.5; 548/335.5
[58] Field of Search ............... 548/336, 337, 339, 342, 548/343, 112, 171, 252, 264.4, 315.1, 316.4, 320.1, 321.1, 322.5, 323.5, 324.1, 325.5, 328.5, 335.5; 514/397, 398, 400, 269, 341, 365, 374, 376, 381, 383, 384; 544/333; 546/278

[56] References Cited

U.S. PATENT DOCUMENTS 4,340,598  7/1982  Furukawa et al. ................ 548/337
4,355,040  10/1982  Furukawa et al. ................ 548/336

FOREIGN PATENT DOCUMENTS 0103647  3/1984  European Pat. Off. .
0245637  11/1987  European Pat. Off. .
0253310  1/1988  European Pat. Off. .
0324377  7/1989  European Pat. Off. .
1341375  12/1973  United Kingdom .

OTHER PUBLICATIONS

Burger, A. *Medicinal Chemistry*, 2nd Ed., New York, pp. 565–571, 578–581, 600–601, (1960).
Denkewalter et al., Progress in Drug Research, vol. 10, pp. 510–512, (1966).

Primary Examiner—Floyd D. Higel
Attorney, Agent, or Firm—Mary E. McCarthy; Stephen Venetianer; Edward T. Lentz

[57] ABSTRACT

Angiotensin II receptor antagonists having the formula:

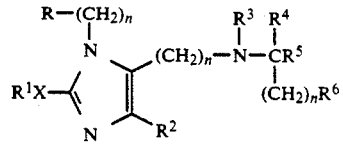

which are useful in regulating hypertension and in the treatment of congestive heart failure, renal failure, and glaucoma, pharmaceutical compositions including these antagonists, and methods of using these compounds to produce angiotensin II receptor antagonism in mammals.

20 Claims, No Drawings

SUBSTITUTED N-(IMIDAZOLYL)ALKYL ALANINE DERIVATIVES

This application is a continuation-in-part of U.S. Ser. No. 07/432,111, filed Nov. 6, 1989, now abandoned.

The present invention relates to new substituted N-(imidazolyl)alkyl alanine derivatives which are angiotensin II receptor antagonists and are useful in regulating hypertension induced or exacerbated by angiotensin II and in the treatment of congestive heart failure, renal failure, and glaucoma. This invention also relates to pharmaceutical compositions containing substituted N-(imidazolyl)alkyl alanine derivatives and methods for using these compounds as antagonists of angiotensin II, as anti-hypertensive agents and and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, stimulates the release of aldosterone from the adrenal cortex. Therefore, the renin angiotensin system, by virtue of its participation in the control of renal sodium handling, plays an important role in cardiovascular homeostasis.

Interruption of the renin-angiotensin system with converting enzyme inhibitors, such as captopril, has proved to be clinically useful in the treatment of hypertension and congestive heart failure (Abrams, W.B., et al., (1984), *Federation Proc.*, 43, 1314). The most direct approach towards inhibition of the renin angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N.K., (1984), *J. Cardiovas. Pharmacol.*, 6, S176). In addition, recent animal studies suggest that inhibition of the renin angiotensin system may be beneficial in halting or slowing the progression of chronic renal failure (Anderson, S., et al., (1985), *J. Clin. Invest.*, 76, 612). Also, a recent patent application (South African Patent Application No. 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure, glaucoma, and other disorders attributed to the actions of AII. When compounds of this invention are administered to mammals, the elevated blood pressure due to AII is reduced and other manifestations based on AII intercession are minimized and controlled. Compounds of this invention are also expected to exhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

U.S. Pat. No. 4,340,598 discloses substituted imidazol-5-yl alkanoic acids, and amido and lower-alkyl ester derivatives thereof, of the formula:

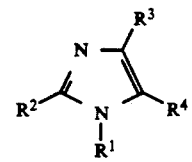

wherein $R^1$ is lower alkyl or phenyl$C_{1-2}$alkyl optionally substituted with halogen or nitro; $R^2$ is lower alkyl, cycloalkyl, or phenyl optionally substituted; one of $R^3$ and $R^4$ is —$(CH_2)_nCOR^5$, where $R^5$ is amino, lower alkoxy or hydroxy and n is 0-2, and the other of $R^3$ and $R^4$ is hydrogen or halogen. Examples include 1-benzyl-2-n-butyl-4-chloro-imidazole-5-acetamide and 1-benzyl-2-n-butyl-5-chloroimidazole-4-acetic acid.

U.S. Pat. No. 4,355,040 discloses substituted 1-benzyl imidazol-5-yl acetic acid derivatives having the formula:

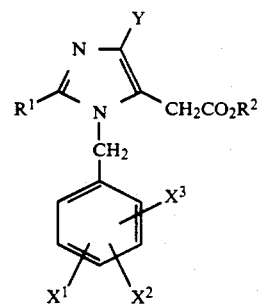

wherein $R^1$ is lower alkyl, cycloalkyl, or phenyl optionally substituted; $X^1$, $X^2$ and $X^3$ are each hydrogen, halogen, nitro, amino, lower alkyl, lower alkoxy, benzyloxy, or hydroxy; Y is halogen and $R^2$ is hydrogen or lower alkyl. A compound specifically disclosed is 1-(2-chlorobenzyl)-2-n-butyl-4-chloroimidazole-5-acetic acid.

European Patent Application 103,647 discloses substituted 1-benzyl-2-phenyl-4-chloro-imidazol-5-yl acetic acid derivatives of the formula:

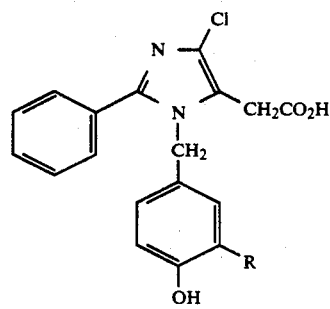

wherein R is lower alkyl. Specifically, the disclosure includes 4-chloro-1-(4-methoxy-3-methylbenzyl)-2 phenylimidazole-5-acetic acid.

European Patent Application 245,637 discloses substituted 4,5,6,7-tetrahydro-1H-imidazo[4,5-c]pyridine derivatives of the formula:

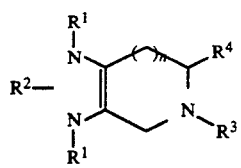

wherein $=$ is a single or double bond; one of $R^1$ is present and includes groups such as $(CH_2)_{1-6}$naphthyl, $(CH_2)_{1-6}$hetero-aryl, or $(CH_2)_{1-6}$Ph optionally substituted; $R^3$ includes groups such as $COC_{1-15}$alkyl or $(CH_2)_{1-6}$Ph optionally substituted; $R_4$ includes $CO_2R^9$, wherein $R^9$ is hydrogen, lower alkyl or benzyl; and n is 0-3. A compound specifically disclosed is 5-[(4-nitrophenyl)acetyl]-1-(phenylmethyl)-4,5,6,7-tetrahydro-1H-imidazo[4,5-c]pyridine-6-carboxylic acid.

European Patent Application 253,310 discloses substituted 1-aralkyl-imidazoles having the general formula:

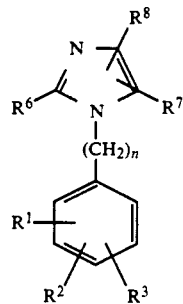

wherein $R^1$ includes groups such as phenyl optionally substituted or adamantylmethyl; $R^2$ includes groups such as hydrogen, halo, $NO_2$, $C_{1-4}$alkyl, or $C_{1-4}$alkoxy; $R^3$ is hydrogen, halo, $C_{1-4}$alkyl, or $C_{1-4}$alkoxy; $R^6$ includes groups such as $C_{2-10}$alkyl, $C_{3-10}$alkenyl, $C_{3-8}$cycloalkyl, benzyl optionally substituted or $Z(CH_2)_{1-5}R^5$, wherein Z is O or S and $R^5$ is hydrogen, $C_{1-6}$alkyl, $C_{3-6}$cycloalkyl or alkenyl; $R^7$ is hydrogen, halo, $NO_2$, $CF_3$, or CN, and $R^8$ includes groups such as $C_{1-10}$alkanoic acids, esters and amides and alkyl N-alkyl carbamates. Examples include 2-n-butyl-5-chloro-1-(4-nitrobenzyl)imidazole-4-acetic acid and methyl 1-[(2′-carboxybiphenyl-4-yl)methyl]-n-butyl-4-chloroimidazole-5-carboxylate.

Great Britain Patent 1,341,375 describes a series of substituted imidazoles which are useful due to their activity at H-1, H-2 and/or other histamine receptors. The substituted aminoalkylimidazole compounds disclosed therein are of the formula:

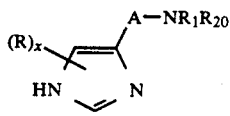

wherein A is $C_{1-6}$ alkyl, optionally substituted by alkyl or aralkyl; R is a substituted or unsubstituted alkyl, aryl, or aralkyl group; $R_1$ is hydrogen, alkyl, phenyl, phenylalkyl or imidazolylalkyl; $R_{20}$ is hydrogen, alkyl optionally substituted by halo, OH, CN, $CO_2H$, $NH_2$, or $CONH_2$; or COY wherein Y is $R_{11}O$ or $R_{11}NH$ and $R_{11}$ is a substituted or unsubstituted alkyl, aryl, aralkyl or amidino group; and X is 0-3. Examples include N-(2-(4(5)-imidazolyl)ethyl)glycine and 1-benzyl-5-(2-aminoethyl)imidazole.

DESCRIPTION OF THE INVENTION

The compounds of the present invention that are blockers of angiotensin II receptors are represented by the following Formula (I):

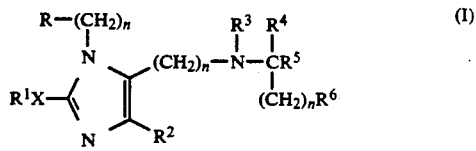

in which:

R is adamantylmethyl, or phenyl, biphenyl, or naphthyl, with each aryl group being unsubstituted or substituted by one to three substituents selected from Cl, Br, F, I, $C_1$-$C_6$alkyl, nitro, $CO_2R^7$, $C_1$-$C_6$alkoxy, hydroxy, $SC_1$-$C_6$alkyl, $SO_2C_1$-$C_6$alkyl, tetrazol-5-yl, $SO_2NHR^7$, $NHSO_2R^7$, $SO_3H$, $PO(OR^7)_2$, $CONR^7R^7$, CN, $NR^7R^7$, $NR^7COH$, $NR^7COC_1$-$C_6$alkyl, $NR^7CON(R^7)_2$, $NR^7COW$, $SO_2W$, or W;

$R^1$ is $C_2$-$C_{10}$alkyl, $C_3$-$C_{10}$alkenyl, $(CH_2)_{0-8}C_3$-$_6$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R^7$, $CO_2R^7$, CN, $CONR^7R^7$, W, $NR^7COH$, $NR^7COC_1$-$C_6$alkyl, $NR^7COW$, $SC_1$-$C_6$alkyl, $SO_2W$, or $SO_2C_1$-$C_6$alkyl;

$R^2$ is hydrogen, Cl, Br, F, I, CHO, hydroxymethyl, $C_1$-$C_6$alkyl, $NR^7R^7$, $CO_2R^7$, $CONR^7R^7$, $NO_2$, CN, phenyl, or W;

X is a single bond, S, or O;

$R^3$ is H, $C_{1-6}$alkyl, $C_{3-6}$alkenyl, $COC_{1-5}$alkyl, or $(CH_2)_{0-3}$phenyl;

$R^4$ is H, $C_{1-6}$alkyl, $C_{3-6}$alkenyl, or $(CH_2)_{0-3}$phenyl;

$R^5$ is $CO_2R^7$, $CONR^7R^7$, or tetrazol-5-yl;

each n independently is 0-4;

$R^6$ is phenyl, naphthyl, 2- or 3-thienyl, 2 or 3-furyl, 2-, 3-, or 4-pyridyl, pyrimidyl, imidazolyl, thiazolyl, triazolyl, triazolyl, tetrazolyl, pyrazolyl, pyrrolyl, oxazolyl, or isoxazolyl, with each aryl or heteroaryl group being unsubstituted or substituted by $C_{1-6}$alkyl, $C_{1-6}$alkoxy. Cl, Br, F, I, $NR^7R^7$, $CO_2R^7$, $CONR^7R^7$, $SO_3H$, $SO_2NHR^7$, OH, $NO_2$ W, $SO_2C_1$-$C_6$alkyl, $SO_2W$, $SC_1$-$C_6$alkyl, $NR^7COH$, $NR^7COW$, or $NR^7COC_1$-$C_6$alkyl;

W is $C_mF_{2m+1}$ wherein m is 1-4; and each $R^7$ independently is H or $C_{1-6}$alkyl; or a pharmaceutically acceptable salt thereof.

Preferred compounds of the invention are represented by Formula (I) wherein:

R is phenyl unsubstituted or substituted by one to three substituents selected from chloro, fluoro, nitro, methyl, trifluoromethyl, methoxy, hydroxy, sulfonamido, sulfamyl, carboxy, carbo$C_{1-4}$alkoxy, carbamoyl, cyano, or tetrazol-5-yl., $R^1$ is $C_{2-8}$alkyl;

X is a single bond or S;

$R^2$ is hydrogen, chloro, fluoro, or trifluoromethyl;

$R^3$ is hydrogen, methyl, or $COC_{1-5}$alkyl;
$R^4$ is hydrogen or $C_{1-3}$alkyl;
$R^5$ is $CO_2H$ or tetrazol-5-yl;
$R^6$ is phenyl or 2-thienyl; and each n independently is one or two;
or a pharmaceutically acceptable salt or hydrate thereof.

As used herein, the terms alkyl, alkenyl, alkoxy, and alkynyl mean carbon chains which are branched or unbranched with the length of the chain determined by the descriptor compounds are the racemic mixtures as well as the single enantiomers encompassed by the genus of Formula (I). The D enantiomers are generally more active and thus are preferred over the L enantiomers.

Particular compounds of the invention include, but are not limited to, the following:

N-[{1-[(2-chlorophenyl)methyl]-2-n-butyl-1H-imidazol-5-yl}methyl]-α-methylphenylalanine,
N-[{1-[(2-chlorophenyl)methyl]-2-n-butyl-1H-imidazol-5-yl}methyl]methyl-β-(2-thienyl) alanine,
N-[{1-[(2chlorophenyl)methyl]-2-n-butyl-1H-imidazol-5-yl}methyl ]-β-(2-thienyl)alanine,
N-[{(1-[(2-chlorophenyl)methyl]-2-n-butyl-1H-imidazol-5-yl}methyl]phenylalanine,
N-[{1-[(2-chlorophenyl)methyl]-2-thiopropyl-1H-imidazol-5-yl}methyl]phenylalanine,
N-[{1-[(2-chlorophenyl)methyl]-2-thiopropyl-1H-imidazol-5-yl}methyl]-N-butyrylphenylalanine,
N-[2-{1-[(2-chlorophenyl)methyl]-2-n-butyl-1H-imidazol-5-yl}methyl]phenylalanine,
N-[2-{1-[(2-chlorophenyl)methyl]-2-n-butyl-1H-imidazol-5-yl}methyl]-β-(2 -thienyl)alanine,
N-[2-{1-[(2-chlorophenyl)methyl]-2-n-butyl-1H-imidazol-5-yl}methyl]-β-(2-thienyl )alanine,
N-[{1-[(2-chlorophenyl)methyl]-2-n-butyl-1H-imidazol-5-yl}methyl]-α-ethylphenylalanine,
N-[{1-[(2-chlorophenyl)methyl]-2-n-butyl-1H-imidazol-5-yl}methyl]-α-propylphenylalanine,
N-[{(1-[(2-chlorophenyl)methyl]-2-n-butyl-1H-imidazol-5yl}methyl]-N-acetylphenylalanine,
N-[{1-[(2-chlorophenyl)methyl]-2-n butyl-1H-imidazol-5-yl}methyl]homophenylalanine,
N-[{-[(2-chlorophenyl)methyl]-2-n-butyl-1H-imidazol-5yl}methyl]-α-methylphenylaline,
N-[{1-[(4-carboxyphenyl)methyl]-2-n-butyl-1H-imidazol-5-yl}methyl]phenylalanine,
N-[{1-[(4-carboxyphenyl)methyl]-2-n-butyl-1H imidazol-5-yl}methyl]-β-(2-thienyl) alanine, and
N-[{1-[(2 chlorophenyl)methyl]-2-n-butyl-1H-imidazol-5-yl}methyl]-N-methylphenylalanine; or a pharmaceutically acceptable salt or hydrate thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of producing antihypertensive activity and methods of treating congestive heart failure, renal failure, and glaucoma by administering these compounds are also included in this invention.

The compounds of this invention and of the pharmaceutical compositions and methods of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule.

The following procedures are useful for the preparation of compounds of Formula (I) particularly where R is 2-chlorophenyl or 4-carboxyphenyl, $R^1$ is n-propyl or n-butyl, X is a single bond or S, $R^2$ is hydrogen chloro, or fluoro, $R^3$ is hydrogen, methyl or $COC_{1-5}$alkyl, $R^4$ is hydrogen or $C_{1-3}$ alkyl, $R^5$ is $CO_2H$ or tetrazol-5-yl, $R^6$ is phenyl or 2-thienyl, and each n independently is one or two.

The starting materials, 2-$R^1$X-imidazole, are known to the art (*J. Org. Chem.* 45:4038, 1980) or are synthesized by known procedures. For example, imidazole is converted to 2 n-butylimidazole by reacting imidazole with triethylorthoformate and p toluenesulfonic acid to give 1-diethoxyorthoamide imidazole and then treating with n-butyl lithium to give the 2-lithium derivative of the orthoamide and alkylating with n-butyl iodide in a suitable solvent, such as tetrahydrofuran (THF).

The 1-R(CH₂)₁₋₄-group is incorporated onto the 2-$R^1$X-imidazole by known procedures, for example, by reaction with a R-(CH₂)₁₋₄ halide, mesylate or acetate, such as 2-chlorobenzyl bromide, in a suitable solvent, such as dimethylformamide (DMF), in the presence of a suitable acid acceptor, such as sodium alkylate, potassium or sodium carbonate, or a metal hydride, preferably sodium hydride at a reaction temperature of 25° C. to 100° C., preferably 50° C. The resulting 1-R(CH₂)₁₋₄-2-$R^1$X-imidazole is hydroxymethylated in the 5-position, for example, by reacting with formaldehyde in the presence of sodium acetate in acetic acid to provide the 1pR(Ch₂)₁₋₄-2-$R^1$X-5-hydroxymethylimidazole intermediates.

Alternatively, the 1-R(CH₂)₁₋₄-2-$R^1$-5-hydroxymethylimidazole intermediates are prepared by reacting an imido ether, $R^1$—C(=NH)-Oalkyl, such as valeramidine methyl ether, with dihydroxyacetone in liquid ammonia under pressure to give 2-$R^1$-5-hydroxymethylimidazole. This diacetate intermediate is N-alkylated, for example using 2-chlorobenzyl triflate, and the resulting 1-R(CH₂)₁₋₄-2-$R^1$-5-acetoxymethylimidazole is treated with aqueous base, such as 10% sodium hydroxide solution, to give the 1-R(CH₂)₁₋₄-2-$R^1$-5-hydroxymethylimidazole intermediate.

Compounds wherein the R group is directly attached to the nitrogen of the imidazole ring are prepared following methods described in U.S. Pat. No. 4,194,049. For example, an appropriately substituted benzylamine is reacted with a $R^1$-nitrile, such as valeronitrile, in the presence of a Lewis Acid, such as hydrochloric acid, zinc chloride, or aluminum chloride, in an inert organic solvent, such as tetrahydrofuran, methylene chloride, or toluene, at a temperature of 25° C. to 150° C. The resulting amidine is converted to the 1-R-2-$R^1$-imidazol-5-carboxaldehyde derivative in a reaction with a halomalonaldehyde, such as bromomalonaldehyde, in an appropriate solvent, such as a $C_1$-$C_4$alkyl alcohol. The 5-hydroxymethylimidazole is prepared by reacting the 5-carboxaldehyde compound with a metal hydride reducing agent, such as sodium borohydride, in an organic solvent, such as a $C_1$-$C_4$ alkyl alcohol.

Alternately, the 2-$R^1$S-imidazole compounds are prepared by the following procedure. Benzylamines, substituted by one to three substituents selected from halo, $C_{1-6}$alkyl, $C_{1-6}$alkoxy, $NO_2$, $SC_{1-6}$alkyl, $SO_2C_{1-6}$alkyl, or $C_mF_{2m+1}$, wherein m is 1–4, are alkylated with a $C_{1-6}$alkyl chloroacetate, for example methyl chloroacetate, in the presence of a base, such as triethylamine, in a suitable solvent, such as dimethylformamide. The resulting alkylaminoalkyl ester compounds are N-formulated with formic acid in the presence of a suitable solvent, such as xylenes, followed by C-formulation of the carbon alpha to both the amino and the ester groups. Reaction of this intermediate with acidic thiocyanate, preferably potassium thiocyanate, in an inert organic solvent, such as $C_{1-4}$alkyl alcohol produces 1-$RCH_2$-2-mercapto-5-alkanoate ester imidazole compounds. The free thio group of the ester imidazole is reacted with a halo-$R^8$ compound, wherein $R^8$ is $C_{2-10}$alkyl, $C_{3-10}$alkenyl, $(CH_2)_{0-8}C_{3-6}$cycloalkyl or an optionally substituted $(CH_2)_{0-8}$phenyl, preferably n-propyl bromide, in the presence of a suitable base, such as sodium carbonate, in an appropriate solvent, such as ethyl acetate. The ester is reduced to the 5-hydroxymethylimidazole intermediate by reduction with a suitable reagent, preferably diisobutyl aluminum hydride, in an appropriate solvent, such as tetrahydrofuran, at a temperature of $-78°$ C. to $25°$ C., preferably at less than $-10°$ C.

The 5-hydroxymethyl group of the hereinbefore described intermediates is reacted with a halogenating agent, such as thionyl chloride, to give a substituted 5-chloromethyl imidazole, which is reacted with an amine of the formula (II):

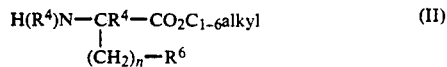

$$H(R^4)N-CR^4-CO_2C_{1-6}alkyl \quad\quad (II)$$
$$\phantom{H(R^4)N-}|$$
$$\phantom{H(R^4)N-}(CH_2)_n-R^6$$

Wherein $R^4$, $R^6$, and n are as defined for Formula (I) compounds. The amine is a D,L-, D-, or L-β-aryl- or β-heteroarylalanine ester, which is reacted with the 5-chloromethyl compound in the presence of a base, such as triethylamine, in a suitable solvent, preferably dimethylformamide, at a temperature of $0°$ C. to $110°$ C., preferably at $90°$ C. Optionally, when the $R^4$ substituent attached to the nitrogen is H, the amine of the above product may be reacted with a $C_{1-5}C(O)$halide, such as butyryl chloride, in the presence of a base, such as triethylamine, in an inert solvent, preferably methylene chloride to give an amide. The resulting substituted Formula (I) ester compounds are hydrolyzed to the corresponding Formula (I) carboxylic acids with aqueous base, such as aqueous potassium or sodium hydroxide, in a suitable solvent, preferably a $C_1-C_4$alkyl alcohol.

Alternatively, the hydroxymethyl group of the 1-$R(CH_2)_n$-2-$R^1X$-5-hydroxymethylimidazole intermediate is oxidized to an aldehyde by treatment with a suitable reagent, such as anhydrous chromic acid-silica gel in tetrahydrofuran or, preferably, with activated manganese dioxide, in a suitable solvent such as benzene, methylene chloride, xylenes or preferably toluene, at a temperature of $25°$ C. to $140°$ C., preferably about $100°$ C. The 1-$R(CH_2)_n$-2-$R^1X$-imidazol-5-carboxaldehydes are reacted with a formula (II) amine compound, as hereinbefore defined, to give an imine compound, which is subjected to reduction using a suitable reagent, such as an alkali borohydride, preferably sodium cyanoborohydride, in an appropriate solvent, such as a $C_1-C_4$ alkyl alcohol, to give Formula (I) ester compounds. The Formula (I) N-acylated and carboxylic acid compounds are prepared as hereinbefore described.

Formula (I) compounds wherein the alkylene bridge at the 5 position of the imidazole ring is defined as n equal to 2 or 3 are prepared from the corresponding alkanoic esters, which are disclosed in U.S. Pat. No. 4,340,598, employing the methods hereinbefore described.

Compounds of Formula (I) in which the R substituent is substituted by hydroxy are formed from Formula (I) compounds in which the R group is substituted by $C_1-C_6$alkoxy using an ether-cleaving reagent, such as boron tribromide or hydrobromic acid.

Compounds of Formula (I) in which the R substituent is substituted by carboxy are formed from Formula (I) compounds in which the R group is substituted by $CO_2C_1-C_6$alkyl using basic hydrolysis, such as aqueous sodium or potassium hydroxide in methanol or ethanol, or using acidic hydrolysis, such as aqueous hydrochloric acid.

Formula (I) tetrazole compounds are prepared by the following procedure. The Formula (I) acid compounds, hereinbefore described, are reacted with a halogenating agent, such as thionyl chloride, in a suitable solvent, for example benzene, to give the corresponding acid halide compounds. The acid halides are then converted to primary amide compounds in a reaction with concentrated ammonia. Subsequent dehydration of the amides with oxalyl chloride/dimethylformamide in acetonitrile/dimethylformamide yields the nitrile compounds, which are the immediate precursors to the Formula (I) tetrazole compounds. Tetrazole formation is accomplished by reacting the nitriles with azide, preferably aluminum azide prepared in situ by the reaction of sodium azide with aluminum chloride, in a suitable solvent, for example tetrahydrofuran.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent, such as ethanol, with isolation of the salt occurring by removal of the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, qlycolic, p-aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I) that have a carboxy group are prepared by known methods from organic and inorganic bases, including non-toxic alkali metal and alkaline earth bases, for example, calcium, lithium, sodium, and potassium hydroxide; ammonium hydroxide, and non-toxic organic bases such as triethylamine, dicyclohexylamine, butylamine, piperazine, meglumine, choline, diethanolamine, and tromethamine.

Angiotensin II antagonist activity of the compounds of Formulas (I) is assessed by in vitro and in vivo methods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

BINDING

The radioligand binding assay is a modification of a method previously described in detail (Gunther et al., Circ. Res. 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the IC$_{50}$ which is the concentration of antagonist needed to displace 50% of the total specifically bound angiotensin II. Exemplary of the IC$_{50}$ of compounds of the invention is about 0.6 to about 30 $\mu$M.

AORTA

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist dissociation constants ($K_B$) are calculated by the dose ratio method using the mean effective concentrations. Exemplary of the $K_B$ of compounds of the invention is about 0.15 to about 15 $\mu$M.

INHIBITION OF PRESSOR RESPONSE TO ANGIOTENSIN II IN CONSCIOUS RATS

Rats are prepared with indwelling femoral arterial and venous catheters and a stomach tube (Gellai et al., KidneyInt. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 3 to 300 mg/kg. The dose of compound needed to produce 50% inhibition of the control response to angiotensin II IC$_{50}$) is used to estimate the potency of the compounds. The IC$_{50}$ of N-[{(1-[(2-chlorophenyl)methyl]-2-n-butyl-1H-imidazol-5-yl}methyl-α-methyl-β-(2-thienyl)alanine is 11mg/kg i.v. and 45 mg/kg orally.

ANTIHYPERTENSIVE ACTIVITY

The antihypertensive activity of the compounds is measured by their ability to reduce mean arterial pressure in conscious rats made renin dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally. The dose of compound needed to reduce mean arterial pressure by 30 mm Hg (IC$_{30}$) is used as an estimate of potency. The IC$_{30}$ of N-[{1-[(2-chlorophenyl)methyl]-2-n-butyl-1H-imidazol-5-yl}methyl-α-methyl-β-(2-thienyl)alanine is 15 mg/kg i.v. and 70 mg/kg orally.

The intraocular pressure lowering effects employed in this invention may be measured by the procedure described by Watkins, et al., J. Ocular Pharmacol., 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmologic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non toxic polymers, for example, cellulose derivatives such as methyl cellulose. The pharmaceutical preparation may also contain non toxic auxiliary substances such as emulsifying, preserving, wetting, and bodying agents, as for example, polyethylene glycols; antibacterial components such as quaternary ammonium compounds; buffering ingredients such as alkali metal chloride; antioxidants such as sodium metabisulfite; and other conventional ingredients such as sorbitan monolaurate.

In addition, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, non-toxic quantity selected from the range of 0.01–200 mg/kg of active compound, preferably 0.1–100 mg/kg. The selected dose is administered to a human patient in need of angiotensin receptor antagonism from 1–6 times daily, orally, rectally, topically, by injection, or continuously by infusion. Oral dosage units for human administration preferably contain from 10 to 500 mg of active compound. Lower dosages are used generally for parenteral administration. Oral administration is used when safe, effective, and convenient for the patient. Topical formulations contain the active compound in an amount selected from 0.0001 to 0.1 (w/v%), preferably 0.0001 to 0.01. As a topical dosage unit form, an amount of active compound from between 50 ng to 0.05 mg, preferably 50 ng to 5 μg is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the methods of treating congestive heart failure, glaucoma, and renal failure comprise administering a compound of Formula (I) to a subject in need of the indicated activity in an effective amount to produce said activity.

The following examples illustrate preparation of compounds and pharmaceutical compositions of this invention. The examples are not intended to limit the scope of this invention as defined hereinabove and as claimed below.

EXAMPLE 1

N-[{1-[(2-Chlorophenyl)methyl]-2-thiopropyl-1H-imidazol-5-yl}methyl]phenylalanine (i)

5-carboxymethyl-1-(2-chlorophenyl)methyl-2-thio-1H-imidazole

A solution of 2-chlorobenzylamine (14.2 g, 0.1 mol) and triethylamine (13.9 ml, 0.1 mol), in dimethylformamide (100 ml) was treated with methyl chloroacetate (10.9 g, 0.1 mol), and the mixture was heated at 50° C. for 3.5 hours. The cooled reaction mixture was diluted with ether, the solids filtered and the concentrated filtrate was flash chromatographed over silica gel with 6:5 hexane in ethyl acetate to provide 15.3 g (71%) of homogeneous methyl 2-[N-(2-chlorophenyl)methyl]-aminoacetate. This product (15.2 g, 0.071 mol) in mixed xylenes (100 ml) was treated with 98% formic acid (2.74 ml, 0.0711 mol) and the mixture was refluxed for 2.5 hours with a Dean-Stark water separator. Evaporation gave 17.1 g (99%) of methyl 2-[N-(2-chlorophenyl)-methyl N-formyl)aminoacetate. This formylated product (17.0 g, 0.071 mol) was dissolved in methyl formate (13.3 ml, 0.216 mol) and added dropwise to a sodium methoxide mixture prepared by adding sodium metal (1.79 g, 0.0778 g-atom) to tetrahydrofuran (325 ml) followed by slow addition of methanol (3.15 ml, 0.0778 mol). The combined mixture was stirred at room temperature for 18 hours, then evaporated to dryness. This crude product was dissolved in 50% aqueous methanol (200 ml), treated with charcoal, filtered and the solution was cooled in ice. Concentrated hydrochloric acid (14.3 ml of 12N, 0.171 mol) was added slowly to this solution followed by a solution of potassium thiocyanate (8.6 g, 0.0885 mol) in water (20 ml). The mixture was heated in an oil bath held at 90° C. for 2.5 hours, then cooled to −10° C. The precipitated solid was filtered, washed with cold ethanol-water and dried at 60° C. to provide 14.7 g (74%) of 5-carboxymethyl-1-(2-chlorophenyl)-methyl-2-thio-1H-imidazole; m.p. 72°-74° C.

(ii)

1-(2-chlorophenyl)methyl-5-carboxymethyl-2-thiopropyl-1H-imidazole

A mixture of 5-carboxymethyl-1-(2-chlorophenyl)-methyl-2-thio-1H-imidazole (2 g, 7.08 mmol), ethyl acetate (20 ml), 5% sodium carbonate solution (40 ml) and propyl bromide (4 ml, 44 mmol) was heated at 60° C. for 18 hours. The organic layer was separated, dried over magnesium sulfate and concentrated to 2.23 g of crude product. Trituration with ether provided 1.63 g (71%) of 5-carboxymethyl-1-(2-chlorophenyl)methyl-2-thiopropyl-1H-imidazole; mp 68°-71° C. (from hexane).

(iii)

N-[{1-[(2-chlorophenyl)methyl]-2-thiopropyl-1H-imidazol-5-yl}methyl]phenylalanine methyl ester A solution of 5-carboxymethyl 1-(2-chlorophenyl)-methyl 2-thiopropyl-1H-imidazole (3.74 g, 11.5 mmol) in dry tetrahydrofuran (50 ml) was cooled to −78° C. under argon, and a solution of diisobutyl aluminum hydride in toluene (30 ml of 1M) was added dropwise. The mixture was stirred at −78° C. for 1.5 hours, then allowed to slowly warm to room temperature. The reaction was quenched by pouring onto iced dilute acetic acid, the product was extracted into methylene chloride and the organic extracts were washed with water, 5% sodium carbonate solution and brine. The dried, concentrated product was a light tan solid (3.32 g). Crystallization from ethanol/water gave 1-(2-chlorophenyl)methyl-5-hydroxymethyl-2-thiopropyl-1H-imidazole; mp 98°-101° C.

A mixture of 1-(2-chlorophenyl)methyl-5-hydroxymethyl-2-thiopropyl-1H-imidazole (10 g, 0.0337 mol) in thionyl chloride (75 ml) was refluxed for one hour, evaporated in vacuo and the residue azeotroped three times with toluene. The solid was triturated with ethyl ether and collected to provide 10.4 g (88%) of the hydrochloride salt of 1 (2-chlorophenyl)methyl-5-chloromethyl-2-thiopropyl-1H-imidazole.

A solution of phenylalanine methyl ester hydrochloride (0.863 g, 4 mmol) in dry dimethylformamide (20 ml) was treated with triethylamine (1.04 g, 10.2 mmol), and then a solution of 1-(2 chlorophenyl)methyl-5-chloromethyl-2-thiopropyl-1H-imidazole hydrochloride (1 g, 2.8 mmol) in dimethylformamide (10 ml). The mixture was heated on the steam bath for 3 hours under argon, poured into water and the product was extracted into ethyl acetate. The water washed, dried, concentrated product was flash chromatographed over silica gel with 15% ethyl acetate in methylene chloride to afford 0.78 g (61%) of N-[{1-[(2-chlorophenyl)methyl]-2-thiopropyl-1H-imidazol-5-yl}methyl]phenylalanine methyl ester as an oil whose NMR was entirely consistent with the structure.

(iv)

N-[{1-[(2-chlorophenyl)methyl]-2-thiopropyl-1H-imidazol-5-yl}methyl]phenylalanine To a solution of N-[{1-[(2-chlorophenyl)methyl]-2-thiopropyl-1H-imidazol-5-yl}methyl] phenylalanine methyl ester (0.78 g, 1.7 mmol) in ethanol (10 ml) was added a solution of potassium hydroxide (0.29 g, 5.1 mmol) in water (4 ml). The mixture was briefly heated to reflux, stirred at room temperature for one hour and the ethanol was evaporated. The aqueous layer was extracted with ether, and then acidified to pH 4 with 10% hydrochloric acid solution. The precipitated product was collected and dried to give 0.4 g (51%) of L-N-[{1-[(2-chlorophenyl)methyl]-2-thiopropyl-1H-imidazol-5-yl }methyl]phenylalanine hemihydrochloride; mp 130°-132° C.

EXAMPLE 2

N-Butyryl-N-[{1-[(2-chlorophenyl)methyl]-2-thiopropyl-1H-imidazol-5-yl}methyl]phenylalanine (i)
N-butyryl-N-[{1-[(2-chlorophenyl)methyl]-2-thiopropyl-1H-imidazol-5-yl}methyl]phenylalanine methyl ester To a solution of N-[{1-[(2-chlorophenyl)methyl]-2-thiopropyl-1-H-imidazol-5-yl}methyl] phenylalanine methyl ester (1.35 g, 2.95 mmol) in methylene chloride (50 ml) and triethylamine (0.448 g, 4.43 mmol) was added butyryl chloride (0.38 g, 3.57 mmol). After being stirred at room temperature for 48 hours, the solvent was evaporated, the residue treated with ethyl acetate and some insoluble material was filtered. The ethyl acetate solution was washed with 5% sodium bicarbonate solution and water, dried and the concentrated product was purified over silica gel with a gradient of ethyl acetate in methylene chloride to give 0.81 g (52%) of the title compound methyl ester as an oil.

(ii)
N-butyryl-N-[{1-[(2-chlorophenyl)methyl]-2-thiopropyl-1H-imidazol-5-yl} methylphenylalanine A solution of N-butyryl-N-[{1-[(2-chlorophenyl)methyl]-2-thiopropyl-1H-imidazol-5-yl}methyl]-phenylalanine methyl ester (1.36 g, 2.58 mmol) in ethanol (20 ml) and a solution of potassium hydroxide (0.436 g, 7.75 mmol) in water (10 ml) were stirred at ambient temperature for 2 hours. The mixture was concentrated under reduced pressure, the aqueous layer was washed with ether, and the aqueous solution was treated with activated charcoal and acidified to pH 3.5 with dilute hydrochloric acid solution. The gummy product was extracted into ethyl acetate, dried with anhydrous magnesium sulfate and concentrated to give 0.7 g (53%) of N-butyryl-N-[{1-[(2-chlorophenyl)methyl]-2-thiopropyl-1 H-imidazol-5-yl}methyl]phenylalanine; mp 70°-74° C.

Alternately, the sodium salt of the acid is isolated directly from the reaction mixture, prior to neutralization. The crude basic reaction solution is applied to a reverse-phase flash column equilibrated with water. The inorganics are washed from the column with water (3 void volumes) and then the product is eluted with a 50:50 mixture of acetonitrile in water. The acetonitrile is removed in vacuo and then the desired sodium salt is obtained after lyophilization.

EXAMPLE 3

N-[{1-[(2-Chlorophenyl)methyl]-2-n-butyl-1H-imidazol-5-yl}methylphenylalanine (i) N-[{1-[(2-chlorophenyl)methyl]-2-n butyl-1H-imidazol-5-yl}methylphenylalanine methyl ester Method A. Imidazole was converted to the 1-diethoxy-orthoamide derivative by the method of Curtis and Brown, J Org. Chem., (1980), 45, 20. Imidazole (12.8 g, 0.19 mol) and 118.4 g (0.8 mol) of triethylorthoformate were reacted in the presence of 1 g of p-toluenesulfonic acid to give 20.6 (61%), bp 65°-70° C. (0.1 mm) of 1-diethoxyorthoamide imidazole. This product (17.0 g, 0.1 mol) was dissolved in dry tetrahydrofuran (250 ml). cooled to −40° C. and n-butyl lithium (0.1 mol, 40 ml of 2.5M in hexane) was added at −40° C. to −35° C. After 15 minutes n-butyl iodide (22.1 g, 0.12 mol) was added at −40° C., and the reaction was stirred overnight at ambient temperature. The reaction was partitioned between ether and 0.3N hydrochloric acid, and the organic layer was repeatedly extracted with dilute hydrochloric acid. The combined aqueous extracts were neutralized with sodium bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 ml) and added dropwise to a solution of sodium methoxide (from sodium hydride (2.31 g, 0.0934 mol) in methanol (250 ml). After one hour the solution was evaporated to dryness, and the sodium salt was taken up in dry dimethylformamide (150 ml) and 2 chlorobenzyl bromide (16.3 g, 0.079 mol) was added. The mixture was heated at 50° C. for 17 hours under argon, poured onto ice water and the product was extracted into ethyl acetate. The extract was washed, dried, and concentrated to give 18.5 g of crude product which was chromatographed over silica gel with 2:1 ethyl acetate/hexane to provide 11.9 g (61%) of 2-n-butyl-1-(2-chlorophenyl)methyl-1-H-imidazole as an oil. Thin layer chromatography on silica gel with 4:1 ethyl acetate/hexane gave an $R_f$ value of 0.59.

A mixture of 2-n-butyl-1-(2-chlorophenyl)methyl-1H-imidazole (95.5 g, 0.384 mol), 37% formaldehyde (500 ml), sodium acetate (80 g) and acetic acid (60 ml) was heated to reflux for 40 hours under argon. The reaction was concentrated in vacuo, and the residue was stirred with 500 ml of 20% sodium hydroxide solution for 4 hours, diluted with water and extracted with methylene chloride. The extract was washed, dried, and concentrated. The crude product (117 g) was flash chromatographed over 600 g of silica gel with a gradient of ethyl acetate to 10% of methanol in ethyl acetate to give 8.3 g of starting material, 24.5 g of a mixture of starting material and product, and 44 g (41%) of 2-n-butyl-1-(2-chlorophenyl)-5-hydroxymethyl-1H-imidazole; mp 86°-88° C. (from ethyl acetate). Further elution provided the bis (4,5-hydroxymethyl) derivative; mp 138°-140° C. (from ethyl acetate).

A solution of 2-n-butyl-1-(2-chlorophenyl)methyl-5-chloromethyl-1H-imidazole hydrochloride (0.6 g, 1.18 mmol), obtained from 2-n-butyl-1-(2-chlorophenyl)-methyl-5-hydroxymethyl-1H-imidazole by the method described in Example 1(iii), was reacted with phenylalanine methyl ester hydrochloride by the method described in Example 1(iii) to give, after chromato-graphy over silica gel with 2:1 methylene chloride/ethyl acetate, 0.244 g (31%) of N-[{1-[(2-chlorophenyl)methyl]-2-n-butyl-1H-imidazol-5-yl}-methyl]phenylalanine methyl ester as an oil.

Method B. A solution of 2-n-butyl-1-(2-chlorophenyl)-methyl-5-hydroxymethyl-1H-imidazole, prepared as in Method A, (5.4 g, 0.0194 mol) in toluene (25 ml) was added to a suspension of activated manganese dioxide (27 g) in toluene (325 ml) and the mixture was heated with a Dean Stark water separator at reflux for one hour, and then the heating was continued at 100° C. for 17 hours. The solids were filtered and the filtrate concentrated. The crude product was flash chromatographed over silica gel with 6:4 hexane/ethyl acetate to afford 4.16 g (78%) of 2-n-butyl-1-(2-chlorophenyl)-methyl-1H-imidazol-5-carboxaldehyde as an oil.

A mixture of 2-n-butyl-1-(2-chlorophenyl)methyl-1H-imidazol-5-carboxaldehyde (6.03 g, 22 mmol), phenylalanine methyl ester hydrochloride (4.93 g, 23 mmol), diisopropylethylamine (2.97 g, 23 mmol) and toluene (300 ml) was refluxed with a Dean Stark water separator under an atmosphere of argon for 18 hours. The solvent was evaporated, ether was added to the residue and diisopropylethylamine hydrochloride was removed by filtration. Evaporation of the ether provided 9.81 g of the crude imine, N-[{2-n-butyl-1-[(2-chlorophenyl)-methyl]-1H-imidazol-5-yl}methylene]phenylalanine methyl ester.

This imine (3.2 g, 7.31 mmol) was dissolved in methanol (50 ml) initially cooled in ice water and sodium cyanoborohydride (0.92 g, 14.62 mmol) was added portionwise over several hours at 25° C. The solvent was evaporated and the residue was dissolved in ethyl acetate and water. The organic layer was washed with 5% sodium bicarbonate solution and water, dried and concentrated to 3.24 g of product whose NMR and TLC was identical to the product obtained by Method A.

Method C. A solution of 2-n-butyl-1-(2-chlorophenyl)-methyl-1H-imidazol-5-carboxaldehyde, prepared as in Method B, (10 mmol) in methanol (50 ml) was treated with the free base of phenylalanine methyl ester (10 mmol) and sodium cyanoborohydride (20 mmol) and gaseous hydrochloric acid in ether to pH 6.5, and this mixture was stirred at 25° C. for 3 days. The workup was the same as described in Method B.

(ii) N-[{1-[(2-chlorophenyl)methyl]-2-n butyl-1H-imidazol-5-yl}methyl]phenylalanine The procedure of Example 2(ii) was followed using 0.232 g (0.53 mmol) of N-[{1-[(2-chlorophenyl)methyl]-2-n-butyl-1H-imidazol-5-yl} methyl]phenylalanine methyl ester to give after workup and drying 0.185 g (82%) of the title compound as a white solid; mp 141°-143° C.

EXAMPLE 4

N-[{1-[(2-Chlorophenyl)methyl]-2-n-butyl-1H-imidazol-5-yl}methyl]-α-methylphenylalanine (i)

N-[[1-[(2-chlorophenyl)methyl]-2-n-butyl-1H-imidazol-5-yl}methyl]-α-methylphenylalanine methyl ester Method A. To a solution of diisopropylamine (1.27 g, 12.6 mmol) in tetrahydrofuran (50 ml) was added n-butyl lithium (5 ml of 2.5M in hexane, 12.6 mmol) at 0° C. After being stirred at 0° C. for 15 minutes, the solution was cooled to −78° C. and a solution of the imine, N [{1-[(2-chlorophenyl)methyl]-2-n-butyl-1H-imidazol-5-yl}methylene]phenylalanine methyl ester (Example 3(i) Method B) (5.51 g, 12.6 mmol) in tetrahydrofuran (35 ml) was added dropwise. The mixture was stirred for 30 minutes at −78° C. under argon and methyl iodide (2.06 q, 14.5 mmol) in tetrahydrofuran (15 ml) was added at 78° C. The mixture was allowed to slowly warm to ambient temperature and then stirred for 18 hours. The solvent was evaporated, the residue dissolved in ethyl acetate, the insoluble materials were filtered and the concentrated product was used without purification to give 8N18 g of N-[{1-[(2-chlorophenyl)-methyl]-2-n-butyl-1H-imidazol-5-yl}methylene]-α-methylphenyl-alanine methyl ester.

This product (8.18 g) was dissolved in methanol (75 ml), cooled to 0° C. and sodium cyanoborohydride (1.4 g, 2.2 mmol) was added portionwise. This mixture was stirred for 48 hours at ambient temperature, concentrated and the residue dissolved in ethyl acetate, washed with 5% sodium bicarbonate solution and water, dried and concentrated to 5.5 g of crude product. Flash chromatography over silica gel with 9:1 ethyl acetate/hexane provided 1.4 g of N-[{1-[(2-chlorophenyl)-methyl]-2-n-butyl-1H-imidazol-5-yl}methyl]-α-methylphenylalanine methyl ester.

Method B. A solution of 2-n butyl-1-(2-chlorophenyl)methyl-1H-imidazol-5-carboxaldehyde (0.264 g, 0.955 mmol in methanol (5 ml) was added to a mixture of α-methylphenylalanine methyl ester hydrochloride (0.44 g, 1.91 mmol), triethylamine (97 mg, 0.955 mmol), sodium cyanoborohydride (252 mg, 4 mmol) and methanol (10 ml) at −10° C. The resulting mixture was stirred at 25° C. for 4 days. The usual work up in ethyl acetate provided a 30% yield of a crude product that was identical (TLC and NMR) to the material from Method A.

(ii)

N-[{1-[(2-chlorophenyl)methyl]-2-n-butyl-1H-imidazol-5-yl}methyl]-α-methylphenylalanine The procedure of Example 3(ii) was followed using N-[{1-[(2-chlorophenyl)methyl]-2-n-butyl-1H-imidazol-5-yl}-methyl]-α-methylphenylalanine methyl ester in place of N-[{1-[(2-chloro-phenyl)methyl]-2-n-butyl-1H-imidazol-5-yl}methyl]phenylalanine methyl ester. The title compound was a white solid; mp 157°-159° C.

EXAMPLE 5

N-[{1-[(2-Chlorophenyl)methyl]-2-n-butyl-1H-imidazol-5-yl}methyl]-β-(2-thienyl)alanine (i)

N-[{1-[(2-chlorophenyl)methyl]-2-n-butyl-1H-imidazol-5-yl}methylene]-β-(2-thienyl) alanine methyl ester A solution of 2-n-butyl-1-[(2-chlorophenyl)methyl]-1H-imidazol-5-carboxaldehyde (0.6 g, 2.12 mmol), β-(2-thienyl)alanine methyl ester (0.4 g, 2.16 mmol) and toluene (25 ml) was refluxed under argon with a Dean-Stark water separator for 8 hours. The solvent was evaporated to an orange-red oil (1.1 g) of the title imine whose NMR was consistent with the structure.

(ii)

N-[{1-[(2-chlorophenyl)methyl]-2-n-butyl-1H-imidazol-5-yl}methyl]-β-(2-thienyl) alanine methyl ester A solution of N-[{1-[(2-chlorophenyl)methyl]-2-n-butyl-1H-imidazol-5-yl}methylene]-β-(2-thienyl)alanine methyl ester (1.1 g) in methanol (15 ml) was cooled to 0° C. and sodium cyanoborohydride (0.55 g) was added portionwise. The mixture was brought to ambient temperature, stirred for 18 hours and then the reaction was quenched with water. The product was extracted into methylene chloride, washed with water, dried and concentrated to 0.84 g of crude material. This was chromatographed over silica gel with methylene chloride to provide 0.46 g (49% calculated from the carboxaldehyde) of N [{1-[(2 chlorophenyl)methyl]-2-n-butyl-1H-imidazol-5-yl}methyl]β-(2-thienyl)alanine methyl ester as an oil.

(iii) N-[{1-[(2 chlorophenyl)methyl]-2-n-butyl-1H-imidazol-5-yl}methyl]-β-(2-thienyl)analine A mixture of the methyl ester (Example 5(ii)) (0.46 g), potassium hydroxide (0.18 g), water (2 ml) and ethanol (3 ml) was stirred at 25° C. for 2 days, the ethanol was evaporated, water (6 ml) was added and dilute hydrochloric acid solution was slowly added dropwise until a precipitate appeared. The suspension was chilled, filtered, and the product was washed with water and air dried to provide 0.34 g of the title compound as a white solid; mp 89°-91° C.

EXAMPLE 6
N-[{1-[(2-Chlorophenyl)methyl]-2-n-butyl-1H-imidazol 5-yl}methyl]-α-methyl-β-(2-thienyl)analine (i)
N-[{1-[(2-chlorophenyl)methyl]-2-n-butyl-1H-imidazol-5-yl}methyl]-α-methyl-β-(2-thienyl)alanine methyl ester The procedure of Example 4(i) (Method A) was followed. From 6.45 g (14.5 mmol) of N-[{1-[(2-chlorophenyl)-methyl]-2-n-butyl-1H -imidazol 5-yl}methylene]-β-(2-thienyl)-alanine methyl ester (Example 5(i)) was obtained 6 g of crude N-[{1-[(2-chlorophenyl)-methyl]-2-n-butyl-1H-imidazol-5-yl}-methylene]-a-methyl-β-(2-thienyl)alanine methyl ester. This imine was reduced according to this procedure but using sodium borohydride (1.1 g) in place of sodium cyanoborohydride to give after chromatography over silica gel with ethyl acetate 2.8 g (34% calculated from two steps). The product is an oil whose NMR was consistent with the structure for N-[{1-[(2-chlorophenyl)methyl]-2-n-butyl-1H-imidazol-5-yl}-methyl]-α-methyl-β-(2-thienyl)alanine methyl ester.

(ii)
N-[{1-[(2-chlorophenyl)methyl]-2-n-butyl-1H-imidazol-5-yl}methyl ]-α-methyl-β-(2-thienyl)alanine The procedure of Example 5(iii) was followed using N-[{1-[(2-chlorophenyl)methyl]-2-n-butyl-1H-imidazol-5-yl}-methyl]-α-methyl-β-(2-thienyl)alanine methyl ester in place of N-[{1-[(2-chlorophenyl)methyl]-2-n-butyl-1H-imidazol -5-yl}methyl]-β-(2-thienyl)alanine methyl ester. The title compound is a white solid; mp 109°-112° C. (from acetonitrile).

EXAMPLE 7
N-[2-{1-[(2-Chlorophenyl)methyl]-2-n-butyl-1H-imidazol-5-yl}ethyl]phenylalanine (i)
2-n-butyl-1-[(2-chlorophenyl)methyl]-5-(2-hydroxyethyl)-1H-imidazole A solution of [2-n-butyl-1-(2-chlorophenyl)methyl-1H-imidazol-5-yl]acetic acid methyl ester (prepared by the method of U.S. Pat. No. 4,340,598) (1.06 g, 3.3 mmol) in tetrahydrofuran (40 ml) was cooled to −78° C. and a solution of diisobutyl aluminum hydride in tetrahydrofuran (9.24 mmol) was added dropwise. The mixture was stirred under argon for 2 hours at −78° C. and then at ambient temperature for 18 hours. With cooling, methanol was added followed by acetic acid (5 ml) and water (20 ml). The mixture was concentrated, and the product was extracted into methylene chloride. The extracts were washed with 5% sodium bicarbonate solution and water. The dried, concentrated solution was chromatographed over silica gel in an ethyl acetate/hexane gradient to give 0.657 g (68%) of 2-n-butyl-1-(2-chlorophenyl)methyl-5-(2-hydroxy)-ethyl-1H-imidazole as an oil.

(ii)
N-[2-{1-[(2-chlorophenyl)methyl]-2-n-butyl-1H-imidazol-5-yl}ethyl]phenylalanine methyl ester A solution of trifluoromethanesulfonic anhydride (0.954 g, 3.38 mmol) in methylene chloride (5 ml) was cooled to −78° C. under nitrogen, and a solution of 2-n-butyl-1-(2-chlorophenyl)methyl-5-(2-hydroxyethyl)-1H-imidazole (0.9 g, 3.07 mmol), diisopropylethylamine (0.44 g. 3.38 mmol) and methylene chloride (10 ml) was added dropwise. The mixture was stirred at −78° C. for an additional 15 minutes, then a solution of the free base of phenylalanine methyl ester (prepared from 1.33 q (6.15 mmol) of the hydrochloride salt) in methylene chloride (10 ml) was added. This mixture was stirred for 2 hours at −78° C. and an additional 18 hours at ambient temperature. The reaction mixture was washed with water, dried and concentrated and the crude product was flash chromatographed with 5% methanol in ethyl acetate to yield 0.9 g (65%) of N-[2-{1-[(2 chlorophenyl)methyl]-2-n-butyl-1H-imidazol-5-yl}ethyl ]phenylalanine methyl ester.

(iii) N-[2-{1 [(2-chlorophenyl)methyl]-2-n-butyl-1H-imidazol-5-yl}ethyl]phenylalanine The procedure of Example 2 (ii) was followed using 0.9 g (1.99 mmol) of N-[2-{1-[(2-chlorophenyl)methyl]-2-n-butyl-1H-imidazol -5-yl}ethyl]phenylalanine methyl ester, 0.33 g of potassium hydroxide, 15 ml of water and 25 ml of ethanol to afford after workup 0.54 q of product. Trituration with ether provided the title compound; mp 78°-80° C. (free base) and mp 232°-233° C. (for the dihydrochloride salt).

EXAMPLE 8
N-[{1-[(2-Chlorophenyl)methyl]-2-n-butyl-4-chloro-1H-imidazol-5-yl}methyl]phenylalanine (i)
2-n-butyl-4-chloro-1-(2-chlorophenyl)methyl-5-hydroxymethyl-1H-imidazole A solution of 2-n-butyl-1-(2-chlorophenyl)methyl-5-hydroxymethyl-1H-imidazole (Example 3(i) Method A) (10.2 g. 0.0368 mol) in tetrahydrofuran (100 ml) was treated portionwise with N-chlorosuccinimide (NCS) (4.92 g, 0.0368 mol) and stirred at 45° C. for a total of 3 hours after the addition of the NCS. The tetrahydrofuran was evaporated and the residue was partitioned between water and ethyl acetate. The organic extracts were washed with water, dried and concentrated to the residual product that crystallized when stirred with ether to yield 5.1 g (44%) of 2-n-butyl 4-chloro 1-(2-chlorophenyl)methyl-5-hydroxymethyl-1H-imidazole; mp 134°-135° C. (from acetonitrile).

(ii) N-[{1-[(2 chlorophenyl)methyl]-2-n-butyl-4-chloro-1H-imidazol-5-yl}methyl]phenylalanine The procedure of Example 3(i), Method A, is followed to prepare the intermediate methyl ester by using 2-n-butyl-4-chloro-1-[(2 chlorophenyl)methyl]-5-chloromethyl-1H-imidazole hydrochloride in place of 2-n-butyl-1-[(2-chlorophenyl)methyl]-5-chloromethyl-1H-imidazole hydrochloride to afford N-[{1-[(2-chlorophenyl)methyl]-2-n-butyl-4-chloro-1H-imidazol-5-yl}methyl]phenylalanine methyl ester. The ester group is hydrolyzed according to the procedure of Example 3 (ii) using N-[{1-[(2-chlorophenyl)methyl]-2-n-butyl-4-chloro-1H-imidazol-5-yl}methyl]phenylalanine methyl ester in place of N-[{1-[(2-chlorophenyl)methyl]-2-n-butyl-1H-imidazol-5-yl}methyl]phenylalanine methyl ester to give the title compound.

EXAMPLE 9

N-[{1-[(2-Chlorophenyl)methyl]-2-n-butyl-1H-imidazol-5-yl}methyl]-β-(3-thienyl)alanine The procedure of Example 5 is followed using β-(3-thienyl)alanine methyl ester in place of β-(2-thienyl)alanine methyl ester to give the title compound.

EXAMPLE 10

N-[{1-(2-[Chlorophenyl)methyl]-2-n-butyl-1H-imidazol-5-yl}methyl]-β-(2-furanyl)alanine The procedure of Example 5 is followed using β-(2-furanyl)alanine methyl ester in place of β-(2-thienyl)-alanine methyl ester to give the title compound.

EXAMPLE 11

N-[{1-[(2-Chlorophenyl)methyl]-2-n-butyl-1H-imidazol-5-yl}methyl]tyrosine

The procedure of Example 5 is followed using tyrosine methyl ester in place of β-(2-thienyl)alanine methyl ester to give the title compound.

EXAMPLE 12

N-[{1-[(2-Chloro-6-fluorophenyl)methyl]-2-n-butyl-1H-imidazol-5-yl}methyl]phenylalanine A solution of 2 n-butylimidazole (3.75 g, 0.03 mol) in dry dimethylformamide (4 ml) was added to sodium hydride (0.95 g) in dimethylformamide (18 ml). After the gas evolution subsided, the mixture was stirred one hour under argon and 2-chloro-6-fluorobenzylchloride (5.5 q, 0.031 mol) in dimethylformamide (7 ml) was added slowly. The mixture was stirred for 17 hours at ambient temperature, diluted with ice water and extracted with ethyl acetate. The washed, dried, concentrated organic layer provided 7.63 g (94%) of 2-n-butyl-1-(2-chloro-6-fluorophenyl)methyl-1H-imidazole whose NMR was consistent with the structure. This material was used without further purification.

The procedures of Example 1(ii iii) were used. From 7.63 g of crude 2-n-butyl-1-(2-chloro-6-fluorophenyl)-methyl-1H-imidazole was obtained 2.8 q of 2-n-butyl-1-(2-chloro-6-fluorophenyl)methyl-5-hydroxymethyl-1H-imidazo le; mp 106°-108° C. (from ethyl acetate). This material was oxidized with manganese dioxide and worked up as described to give 0.88 g (63%) of 2-n butyl-2-(2-chloro-6-fluorophenyl)methyl-1H-imidazol-5-carboxaldehyde; mp 88°-90° C. (from ethyl acetate).

The title compound is prepared according to Example 3 using 2-n-butyl 1-(2-chloro-6 fluorophenyl)methyl-1H-imidazol-5-carboxaldehyde in place of 2-n-butyl-1-(2-chlorophenyl)methyl-1H-imidazol-5-carboxaldehyde.

EXAMPLE 13

N-[2-{1-[(2-Chlorophenyl)methyl]-2-n-butyl-1H-imidazol-5-yl}ethyl]-β-(2-thienyl)alanine The procedure of Example 7 was followed using β-(2-thienyl)alanine methyl ester in place of phenylalanine methyl ester to give the title compound as the dihydrochloride salt; mp 227°-228° C.

EXAMPLE 14

N-[2-{1-[(2-Chlorophenyl)methyl]-2-n-butyl-1H-imidazol-5-yl}ethyl]-α-methyl-β-(2-thienyl)alanine The procedure of Example 7 is followed using α-methyl-β-(2-thienyl)alanine methyl ester in place of phenylalanine methyl ester to give the title compound.

EXAMPLE 15

N-[2-{1-[(2-Chlorophenyl)methyl]-2-n-butyl-1H-imidazol-5-yl}ethyl]-α-ethylphenylalanine The procedure of Example 4 (i), Method A, was followed using a-ethylphenylalanine methyl ester in place of α-methyl-phenylalanine methyl ester to give N-[{1-(2-chlorophenyl)methyl]-2-n butyl-1H-imidazol-5-yl}methyl-α-ethylphenylalanine methyl ester. Hydrolysis of the ester using the procedure of Example 2 (ii), followed by treatment with hydrochloric acid, gave the title compound as the dihydrochloride salt; mp 209°-211° C.

EXAMPLE 16

N-[2-{1-[(2-Chlorophenyl)methyl]-2-n-butyl-1H-imidazol-5-yl}ethyl]-α-propylphenylalanine The procedures of Example 15 were followed using α-propylphenylalanine methyl ester in place of α-ethylphenylalanine methyl ester to give the dihydrochloride salt of the title compound; mp 208°-210° C.

EXAMPLE 17

N-[2-{1-[(2-Chlorophenyl)methyl]-2-n-butyl-1H-imidazol-5-yl}ethyl]-N-acetylphenylalanine N-[{1-[(2-Chlorophenyl)methyl]-2-n-butyl-1H-imidazol-5-yl}methyl]phenylalanine methyl ester (prepared in Example 3(i) Method A) was treated with acetic anhydride at room temperature to give the N-acetyl phenylalanine methyl ester of the title compound. Hydrolysis of the ester following the procedure of Example 2(ii) gave the title compound as an amorphous solid.

EXAMPLE 18

N-[{1-[(2 Chlorophenyl)methyl]-2-n-butyl-1H-imidazol-5-yl}ethyl]homophenylalanine The procedures of Example 3(i), Method B, and 2(ii) were followed using homophenylalanine methyl ester hydrochloride in place of phenylalanine methyl ester hydrochloride to give the title compound as a monohydrate; mp 123° C. (softens).

EXAMPLE 19

N-[{1-[(2-Chlorophenyl)methyl]-2-n-butyl-1H-imidazol 5-yl}ethyl]-α-methylphenylalanine The procedure of Example 7 was followed using α-methylphenylalanine methyl ester in place of phenyl alanine methyl ester to give the title compound as the dihydrochloride salt; 253.5°–255° C.

EXAMPLE 20

N-[{1-[(2-Chlorophenyl)methyl]-2-n-butyl-1H-imidazol-5-yl}ethyl]-N-methylphenylalanine N-[{1-[(2-Chlorophenyl)methyl]-2-n-butyl-1H-imidazol-5-yl}methyl]phenylalanine methyl ester (prepared in Example 3(i) method B) (o.52 g, 1.18 mmol), 88% formic acid (0.31 g), and 37% aqueous formaldehyde (o.44 g) were heated over a steam bath for 18 hours. The reaction mixture was poured into 10% hydrochloric acid solution and then extracted with diethyl ether. The aqueous layer was basified to pH 10 with 10% sodium hydroxide solution and then the product was extracted into ethyl acetate. The organic extract was dried with anhydrous magnesium sulfate and the solvent was removed in vacuo. The crude product was chromatographed on silica gel with 50% ethyl acetate in hexane to give 0.377 g (70%) of N-[{1-[(2-chlorophenyl)methyl]-2-n-butyl-1H-imidazol -5-yl}methyl]-N-methylphenylalanine methyl ester. Hydrolysis of the ester following the procedure of Example 2(ii) gave the title compound as a foam (0.265 g, 77%); mp 59°–61° C.

EXAMPLE 21

N-[{1-[(2-Methylphenyl)methyl]-2-n-butyl-1H-imidazol-5-yl}methyl]phenylalanine

The title compound is prepared following the procedure of Example 3 using 2 methylbenzyl bromide in place of 2-chlorobenzyl bromide.

EXAMPLE 22

N-[{1 [(2 Methylphenyl)methyl]-2-n-butyl 1H-imidazol 5 yl}methyl]phenylalanine

The title compound is prepared following the procedure of Example 3 using 3-methoxybenzyl bromide in place of 2-chlorobenzyl bromide.

EXAMPLE 23

N-[{1-[(4-Phenylphenyl)methyl]-2-n-butyl-1H-imidazol-5-yl}methyl]phenylalanine

The title compound is prepared following the procedure of Example 3 using 4 phenylbenzyl bromide in place of 2-chlorobenzyl bromide.

EXAMPLE 24

N-[{1-[(4-Methoxy-3-methylphenyl)methyl]-2-n-butyl-1H-imidazol 5 yl}methyl]phenylalanine The title compound is prepared following the procedure of Example 3 using 4-methoxy-3-methylbenzyl bromide in place of 2-chlorobenzyl bromide.

EXAMPLE 25

N-[{1-[(2-(1-Adamantyl)ethyl]-2-n-butyl-1H-imidazol-5-yl}methyl]phenylalanine

A mixture of 2-(1-adamantyl)ethanol (10.7 g) and diisopropylethylamine (11 ml) in methylene chloride (70 ml) was added to triflic anhydride (16.75 g) in 70 ml of methylene chloride at −78° C. for 45 minutes, 1-acetyl-2-n-butyl 5-acetoxymethyl imidazole in 50 ml of methylene chloride was added and the mixture was allowed to stand at room temperature for 4 days, then concentrated and heated on a steam bath with 10% sodium hydroxide (250 ml), diluted with 300 ml of water, extracted with methylene chloride, dried, filtered and concentrated to give an oil. Chromatography on silica gel in methanol/chloroform gave 5-acetoxymethyl-1-[2-(1-adamantyl)-ethyl]-2-n-butyl-imidazole. This acetoxy compound (5.4 g) was stirred at room temperature with potassium hydroxide (5.2 g) in ethanol (200 ml) for one hour, the mixture was concentrated, poured into water, stirred, and filtered to give 1-[2-(1-adamantyl)ethyl]-2-n-butyl-5-hydroxymethyl-1H-imidazole.

The title compound was prepared following the procedures of Example 3(i), Method A, and 3(ii) using 1-[2-(1-adamantyl)ethyl]-2-n-butyl-5-hydroxymethyl-1H-imidazole in place of 2-n-butyl-1-(2-chlorophenyl)-methyl-5-hydroxymethyl-1H-imidazole.

EXAMPLE 26

N-[{1-[(3-Chlorophenyl)methyl]-2-n-butyl-1H-imidazol-5-yl}methyl]phenylalanine

The title compound is prepared following the procedure of Example 3 using 3-chlorobenzyl bromide in place of 2-chlorobenzyl bromide.

EXAMPLE 27

N-[{1-[(2-Bromophenyl)methyl]-2-n-butyl-1H-imidazol-5-yl}methyl]phenylalanine

The title compound is prepared following the procedure of Example 3 using 2 bromobenzyl bromide in place of 2-chlorobenzyl bromide.

EXAMPLE 28

N-[{1 [(2 Cyanophenyl)methyl]-2-n-butyl-1H-imidazol-5-yl}methyl]phenylalanine

The title compound is prepared following the procedure of Example 3 using α-bromo-o-tolunitrile in place of 2-chlorobenzyl bromide.

EXAMPLE 29

N-[{1-[(4-Cyanophenyl)methyl]-2-n-butyl-1H-imidazol-5-yl}methyl]phenylalanine

The title compound is prepared following the procedure of Example 3 using α-bromo-p-tolunitrile in place of 2-chlorobenzyl bromide.

EXAMPLE 30

N-[{1 [(2-Nitrophenyl)methyl]-2-n butyl-1H-imidazol-5-yl}methyl]phenylalanine

The title compound is prepared following the procedure of Example 3 using 2-nitrobenzyl bromide in place of 2-chlorobenzyl bromide.

EXAMPLE 31

N-[{1-[(3-Trifluoromethylphenyl)methyl]-2-n-butyl-1H-imidazol-5-yl}methyl]phenylalanine The title compound is prepared following the procedure of Example 3 using α-bromo α,α,α-trifluoro-m-xylene in place of 2-chlorobenzyl bromide.

EXAMPLE 32

N-[{1-[(2-Chlorophenyl)methyl]-2-thiopropenyl-1H-imidazol 5-yl}methyl]phenylalanine The title compound is prepared following the procedure of Example 1 using allyl bromide in place of propyl bromide.

EXAMPLE 33

N-[{1-[(2-Chlorophenyl)methyl]-2-propenyl-1H-imidazol-5-yl}methyl]phenylalanine

The title compound is prepared following the procedure of Example 3 using allyl iodide in place of n-butyl iodide.

EXAMPLE 34

N-[{1-[(2 Chlorophenyl)methyl]-2-thiopentyl-1H-imidazol-5-yl}methyl]phenylalanine The title compound is prepared following the procedure of Example 1 using 1-bromopentane in place of propyl bromide.

EXAMPLE 35

N-[{1-[(2 Chlorophenyl)methyl]-2-thiobenzyl-1H-imidazol-5-yl}methyl]phenylalanine The title compound is prepared following the procedure of Example 1 using benzyl bromide in place of propyl bromide.

EXAMPLE 36

N-[{1-[(2-Chlorophenyl)methyl]-2-thiocyclohexyl-1H-imidazol-5-yl}methyl]phenylalanine The title compound is prepared following the procedure of Example 1 using cyclohexyl bromide in place of propyl bromide.

EXAMPLE 37

N-[{1-[(2-Chlorophenyl)methyl]-2-n-butyl-4-phenyl-1H-imidazol-5-yl}ethyl]phenylalanine The title compound is prepared following the procedure of Example 7 using [2-n-butyl-1-(2-chlorophenyl)-methyl-4-phenyl-1H-imidazol-5-yl]acetic acid methyl ester (prepared by the method of U.S. Pat. No. 4,340,598) in place of [2-n-butyl-1-(2-chlorophenyl)-methyl-1H-imidazol-5-yl]acetic acid methyl ester.

EXAMPLE 38

N-[{1-[(2-Chlorophenyl)methyl]-2-thioheptyl-1H-imidazol-5-yl]methyl]phenylalanine The title compound is prepared following the procedure of Example 1 using 1 bromoheptane in place of propyl bromide.

EXAMPLE 39

N-[{1-[(2-Chlorophenyl)methyl]-2-thiohexenyl-1H-imidazol-5-yl}methyl]phenylalanine The title compound is prepared following the procedure of Example 1 using 6-bromo-1 hexene in place of propyl bromide.

EXAMPLE 40

N-[{1-[(2-Chlorophenyl)methyl]-2-thiocyclopropyl-1H-imidazol-5-yl}methyl]phenylalanine The title compound is prepared following the procedure of Example 1 using cyclopropyl bromide in place of propyl bromide.

EXAMPLE 41

N-[{1 [(2-Nitrophenyl)methyl]-2-n-butyl-1H-imidazole 5-yl}methyl]phenylalanine

The title compound is prepared following the procedure of Example 3 using 2-nitrobenzyl bromide in place of 2-chlorobenzyl bromide.

EXAMPLE 42

N-[{1-(2-Trifluoromethylphenyl)methyl]-2-n-butyl-1H-imidazol-5-yl}-methyl]phenylalanine The title compound is prepared following the procedure of Example 3 using 2 trifluoromethylbenzyl bromide in place of 2 chlorobenzyl bromide.

EXAMPLE 43

N-[{1-[(2,3 Dichlorophenyl)methyl]-2-n-butyl-1H-imidazol-5-yl]methyl]phenylalanine The title compound is prepared following the procedure of Example 3 using 2,3-dichlorobenzyl bromide in place of 2-chlorobenzyl bromide.

EXAMPLE 44

N-[{1-[(2-Methoxyphenyl)methyl]-2-n-butyl-1H-imidazol-5-yl}methyl]phenylalanine

The title compound is prepared following the procedure of Example 3 using 2 methoxybenzyl bromide in place of 2-chlorobenzyl bromide.

EXAMPLE 45

N-[{1-[(3-Methoxyphenyl)methyl]-2-n-butyl-1H-imidazol-5-yl}methyl]phenylalanine

The title compound is prepared following the procedure of Example 3 using 3-methoxybenzyl bromide in place of 2 chlorobenzyl bromide.

EXAMPLE 46

N-[{1 [(2-Chorophenyl)methyl]-2-n butyl-1H-imidazol-5-yl}methyl]-α-2-(thienyl)methyl-α-(1H tetrazol-5-yl)methanamine To a suspension of N-[{1-[(2 chlorophenyl)methyl]-2-n-butyl-1H-imidazol-5-yl}methyl-β-(2-thienyl)alanine, prepared as in Example 5, (4.3 mmol) in benzene (20 ml) is added thionyl chloride (12.9 mmol). The resultant mixture is heated to 50° C. for 90 minutes, then evaporated to any oily residue. The residue is taken up in hexane and evaporated again. The acid chloride is treated with concentrated ammonium hydroxide (40 ml) and then the reaction mixture is stirred for 16 hours at room temperature. The solid is filtered, washed with water, and dried at 50° C. under vacuum to yield the primary amide.

To a solution of dimethylformamide (14.2 mmol) in acetonitrile (50 ml) is added oxalyl chloride (98%, 13.5 mmol) at 0° C. under argon. After 3 minutes, a solution of the amide prepared above in dimethylformamide (20 ml) is added via a cannula. Five minutes later, pyridine (27.2 mmol) is added; the reaction mixture is stirred for an additional 5 minutes at 0° C., then partitioned between ethyl acetate and 50% aqueous ammonium chloride. The ethyl acetate layer is washed with water and brine. The ethyl acetate extract is dried with anhydrous sodium sulfate and evaporated to give the corresponding nitrile derivative.

Tetrahydrofuran (16 ml) is added under argon with stirring to a mixture of the nitrile prepared above (6.44 mmol) and aluminum chloride (13.0 mmol). Sodium azide 58.3 mmol) is added all at once, followed by a 2 ml tetrahydrofuran rinse, and the reaction is heated to 65° C. for 22 hours, then cooled to room temperature. The reaction mixture is diluted with ethyl acetate (20 ml) and treated with 10% hydrochloric acid solution (20 ml) with vigorous stirring for 5 minutes. The ethyl acetate layer is washed with water and brine. The ethyl acetate layer is dried with anhydrous sodium sulfate and evaporated to give N-[{1-[(2-chlorophenyl)methyl]-2-n-butyl-1H-imidazol-5-yl}methyl]-α-(2-thienyl)methyl-α-(1H-tetrazol-5-yl)methanamine.

EXAMPLE 47

N-[{1-[(2,3-Dichlorophenyl)methyl]-2-n butyl-1H-imidazol-5-yl}methyl-α-(phenyl)methyl-α-(1H tetrazol-5-yl)methanamine The title compound is prepared following the procedure of Example 46 using N-[{1-[2,3-dichlorophenyl)-methyl-2-n-butyl-1H-imidazol-5-yl}methyl]phenylalanine, prepared as in Example 43, in place of N-[{1-[(2-chlorophenyl)methyl]-2-n-butyl-1H-imidazol-5-yl}methyl-β-(2-thienyl)alanine.

EXAMPLE 48

N-[{1-[(2-Nitrophenyl)methyl]-2-n-butyl-1H-imidazol-5-yl}methyl-α-(phenyl)methyl-α-(1H-tetrazol-5-yl)methanamine The title compound is prepared following the procedure of Example 46 using N-[{1-[(2-nitrophenyl)methyl]-2-n-butyl-1H-imidazol-5-yl}methyl]phenylalanine, prepared as in Example 41, in place of N-[{1-[(2-chlorophenyl)-methyl]-2-n-butyl-1H-imidazol-5-yl}methyl -β-(2-thienyl)alanine.

EXAMPLE 49

N-[{1-[(2-Chlorophenyl)methyl]-2-n-butyl-1H-imidazol-5-yl}ethyl -α-(phenyl)methyl-α-(1H-tetrazol-5-yl)methanamine The title compound is prepared following the procedure of Example 46 using N-[2-{1-[(2-chlorophenyl)methyl]-2-n-butyl-1H-imidazol-5-yl}ethyl]phenylalanine prepared as in Example 7, in place of N-[{1-[(2-chlorophenyl)methyl]-2-n-butyl-1H-imidazol-5-yl}methyl-β-(2-thienyl)alanine.

EXAMPLE 50

N-[{1 [(2-Chlorophenyl)methyl]-2-n-butyl-1H-imidazol-5-yl}methyl-α-(3-thienyl)methyl-α-(1H-tetrazol-5 yl)methanamine The title compound is prepared following the procedure of Example 46 using N-[{1-[(2-chlorophenyl)methyl-2-n-butyl-1H-imidazol-5-yl}methyl 8-(3-thienyl)alanine, prepared as in Example 9, in place of N-[{1-[(2 chlorophenyl)methyl]-2-n-butyl-1H-imidazol -5-yl}methyl-β-(2thienyl)alanine.

EXAMPLE 51

N-[{1-[(2-Chlorophenyl)methyl]-2-n butyl-1H-imidazol-5-yl}methyl-α-(phenyl)methyl-α-(1H-tetrazol-5-yl)methanamine The title compound is prepared following the procedure of Example 46 using N-[{1-[(2-chlorophenyl)methyl]-2-n-butyl-1H-imidazol-5-yl}methyl]phenylalanine, prepared as in Example 3, in place of N [{(1-[2-chlorophenyl)methyl-2-n-butyl-1H-imidazol-5-yl}methyl-β-(2-thienyl)alanine.

EXAMPLE 52

N-[{1-[(2-Chlorophenyl)methyl]-2-n-butyl-1H-imidazol-5-yl}methyl-α-(2-furanyl)methyl-α-(1H-tetrazol-5-yl)methanamine The title compound is prepared following the procedure of Example 46 using N-[{1-[(2-chlorophenyl)methyl]-2-n-butyl-1H-imidazol-5-yl}β-(2-furanyl)alanine, prepared as in Example 10, in place of N-[{1-[(2-chlorophenyl)methyl]-2-n-butyl-1H imidazol -5-yl}methyl-β-(2-thienyl)alanine.

EXAMPLE 53

N-[{1-[(4-Carboxyphenyl)methyl]-2-n-butyl-1H-imidazol-5-yl}methyl]-β-(2-thienyl)alanine The title compound was prepared following the procedure of Example 3 [(i) method B and (ii)] replacing 2-chlorobenzyl bromide with 4-carbomethoxybenzyl bromide, phenylalanine methyl ester with β-(2-thienyl)alanine methyl ester and sodium cyanoborohydride with sodium borohydride; mp 151°–152° C.

EXAMPLE 54

L-N-[{1-[(4-Carboxyphenyl)methyl]-2-n-butyl-1H-imidazol-5-yl}]phenylalanine

The title compound was prepared following the procedure of Example 3 [(1) Method A and (ii)] replacing 2-chlorobenzyl bromide with 4-carbomethoxybenzyl bromide and phenylalanine methyl ester with L-phenylalanine methyl ester; $[\alpha]^{25} = +32.5$ (methanol); mp 231°–232° C. (hydrochloric acid salt).

EXAMPLE 55

D-N-[{1-[(4-Carboxyphenyl)methyl]-2-n-butyl-1H-imidazol-5-yl}methyl]phenylalanine The title compound is prepared following the procedure of Example 3 [(i) Method A and (ii)] replacing 2-chlorobenzyl bromide with 4-carbomethoxybenzyl bromide and phenylalanine methyl ester with D-phenylalanine methyl ester; $[\alpha]^{25} = -28.9$ (methanol); mp 232°–233° C. (hydrochloric acid salt).

EXAMPLE 56

N-[2-{1-[(4-carboxyphenyl)methyl]-2-n-butyl-1H-imidazol-5-yl}ethyl]-8-(2-thienyl)alanine The title compound is prepared following the procedure of Example 7 replacing [2-n-butyl-1-(2-chlorophenyl)methyl-1H-imidazol-5-yl]acetic acid methyl ester with [2-n-butyl-1-(4-carbomethoxyphenyl)methyl-1H-imidazol-5-yl]acetic acid methyl ester.

EXAMPLE 57

An oral dosage form for administering orally active Formula (I) compounds is produced by screening, mixing and filling into hard gelatin capsules the ingredients in proportions, for example, as shown below.

| Ingredients | Amounts |
| --- | --- |
| N-[{1[(2-chlorophenyl)methyl]-2-n-butyl-1H-imidazol-5-yl}methyl]-a-methyl-β-(2-thienyl)alanine | 100 mg |

-continued

| Ingredients | Amounts |
| --- | --- |
| magnesium stearate | 10 mg |
| lactose | 100 mg |

EXAMPLE 58

The sucrose, calcium sulfate dihydrate and orally active Formula (I) compounds are mixed and granulated with a 10% gelatin solution. The wet branules are screened, dried, mixed with the starch, talc, and stearic acid, screened and compressed into a tablet.

| Ingredients | Amounts |
| --- | --- |
| N-[{1-[(2-chlorophenyl)methyl]-2-n-butyl-1H-imidazol-5-yl}-methyl]-$\beta$-(2-thienyl)alanine | 75 mg |
| calcium sulfate dihydrate | 100 mg |
| sucrose | 15 mg |
| starch | 8 mg |
| talc | 4 mg |
| stearic acid | 2 mg |

EXAMPLE 59

N-[{1-[(2-chlorophenyl)methyl]-2-n-butyl-1H-imidazol-5-yl}methyl]-$\alpha$-methylphenylalanine, 50 mg, is dispersed in 25 ml of normal saline to prepare an injectable preparation.

EXAMPLE 60

A topical ophthalmological solution for administering Formula (I) compounds is produced by mixing under sterile conditions the ingredients in proportions, for example, as shown below.

| Ingredients | Amounts (mg/ml) |
| --- | --- |
| N-[{1-[(2-chlorophenyl)methyl]-2-n-butyl-1H-imidazol-5-yl}methyl]-phenylalanine | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 ml |
| 1.0 N sodium hydroxide | q.s. ad pH 7.4 |

It is to be understood that the invention is not limited to the embodiments illustrated hereabove and the right to the illustrated embodiments and all modifications coming within the scope of the following claims is reserved.

What is claimed is:

1. A compound of the formula:

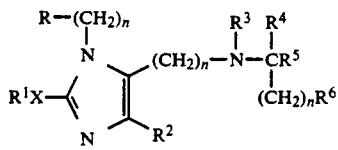

in which:

R is adamantylmethyl, or phenyl, biphenyl, or naphthyl, with each aryl group being unsubstituted or substituted by one to three substituents selected from Cl, Br, F, I, $C_1$-$C_6$alkyl, nitro, $CO_2R^7$, $C_1$-$C_6$alkoxy, hydroxy, $SC_1$-$C_6$alkyl, $SO_1C_1$-$C_6$alkyl, tetrazol-5-yl, $SO_2NHR^7$, $NHSO_2R^7$, $SO_3H$, $PO(OR)_2$, $CONR^7R^7$, CN, $NR^7R^7$, $NR^7COH$, $NR^7COC_1$-$C_6$alkyl $NR^7CON(R^7)_2$, $NR^7COW$, $SO_2W$, or W;

$R^1$ is $C_2$-$C_{10}$alkyl, $C_3$-$C_{10}$alkenyl, $(CH_2)_{0-8}C_{3-6}$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R$, $CO_2R^7$, CN, $CONR^7R^7$, W, $NR^7COH$, $NR^7COC_1$-$C_6$alkyl, $NR^7COW$, $SC_1$-$C_6$alkyl, $SO_2C_1$-$C_6$alkyl, or $SO_2W$;

$R^2$ is hydrogen. Cl, Br, F, I, CHO, hydroxymethyl, $C_1$-$C_6$alkyl, $NR^7R^7$, $CO_2R^7$, $CONR^7R^7$, $NO_2$, CN, phenyl, or W;

X is a single bond, S, or O;

$R^3$ is H, $C_{1-6}$alkyl, $C_{3-6}$alkenyl, $COC_{1-5}$alkyl, or $(CH_2)_{0-3}$phenyl;

$R^4$ is H, $C_{1-6}$alkyl, $C_{3-6}$alkenyl, or $(CH_2)_{0-3}$-phenyl;

$R^5$ is $CO_2R^7$, $CONR^7R^7$, or tetrazol-5-yl;

each n independently is 0–4;

$R^6$ is phenyl, naphthyl, 2- or 3-thienyl, 2- or 3-furyl, 2-, 3-, or 4-pyridyl, pyrimidyl, imidazolyl, thiazolyl, triazolyl, tetrazolyl, pyrazolyl, pyrrolyl, oxazolyl, or isoxazolyl, with each aryl or heteroaryl group being unsubstituted or substituted by $C_{1-6}$alkyl, $C_{1-6}$alkoxy, Cl, Br, F, I, $NR^7R^7$, $CO_2R^7$, $CONR^7R^7$, $SO_3H$, $SO_2NHR^7$, OH, $NO_2$ W, $SO_2C_1$-$C_6$alkyl, $SO_2W$, $SC_1$-$C_6$alkyl, $NR^7COH$, NR COW, or $NR^7COC_1$-$C_6$alkyl;

W is $C_mF_{2m+1}$, wherein m is 1–4; and each $R^7$ independently is H or $C_{1-6}$alkyl;

or a pharmaceutically acceptable salt thereof.

2. A compound of claim 1 in which:

R is phenyl unsbstituted or substituted by one to three substituents selected from chloro, fluoro, nitro, methyl, trifluoromethyl, methoxy, hydroxy, sulfonamido, sulfamyl, cyano, carboxy, carbo$C_{1-6}$alkoxy, carbamoyl, or tetrazol-5-yl;

$R^1$ is $C_{2-8}$alkyl;

X is a single bond or S;

$R^2$ is hydrogen, chloro, fluoro, or trifluoromethyl;

$R^3$ is hydrogen, methyl, or $COC_{1-5}$alkyl;

$R^4$ is hydrogen or $C_{1-3}$alkyl;

$R^5$ is $CO_2H$ or tetrazol 5-yl;

$R^6$ is phenyl or 2-thienyl and;

each n independently is one or two;

or a pharmaceutically acceptable salt thereof.

3. A compound of claim 2 which is N-[{1-[(4-carboxyphenyl)methyl]-2-n-butyl-1H-imidazol-5-yl}methyl]-phenylalanine or a pharmaceutically acceptable salt thereof.

4. A compound of claim 2 which is N-[{1-[(4-carboxyphenyl)methyl]-2-n-butyl-1H-imidazol-5-yl}methyl]-$\beta$-(2-thienyl)alanine or a pharmaceutically acceptable salt thereof.

5. A compound of claim 2 which is N-[{1-[(2-chloro)methyl]-2-n-butyl-1H-imidazol-5-yl}methyl]-$\beta$-(2-thienyl)alanine or a pharmaceutically acceptable salt thereof.

6. A compound of claim 2 which is:

N-[{1-[(2-chlorophenyl)methyl]-2-n-butyl-1H-imidazol-5-yl}methyl]-$\alpha$-methylphenylalanine;

N-[{1-[(2-chloro-phenyl)methyl]-2-n-butyl-1H-imidazol-5-yl}methyl]-$\alpha$-methyl-$\beta$-(2-thienyl)alanine;

N-[{1-[(2-chlorophenyl)methyl]-2-n-butyl-1H-imidazol-5-yl}methyl]phenylalanine;

N-[{1-[(2-chlorophenyl)methyl]-2-thiopropyl-1H-imidazol-5-yl}methyl]-N-butyrylphenylalanine;

N-[{1-[(2-chlorophenyl)methyl]-2-n-butyl-1H-imidazol-5-yl}methyl]-N-butyrylphenylalanine;

N-[2-{1-[(2-chlorophenyl)methyl]-2-n-butyl-1H-imidazol-5-yl}ethyl]-phenyl)alanine;

N-[2-{1-[(2-chlorophenyl)methyl]-2-n-butyl-1H-imidazol-5-yl}methyl]-β-(2-thienyl)alanine;

N-[2-{1-[(2-chlorophenyl)methyl]-2-n-butyl-1H-imidazol-5-yl}methyl]-β-(2-thienyl)alanine;

N-[{1-[(2-chlorophenyl)methyl]-2-n-butyl-1H-imidazolyl-5-yl}methyl]-α-ethylphenylalanine;

N-[{1-[(2-chlorophenyl)methyl]-2-n-butyl-1H-imidazol-5-yl}methyl]-α-propylphenylalanine;

N-[{1-[(2-chlorophenyl)methyl]-2-n-butyl-1H-imidazol-5-yl}methyl]-N-acetylphenylalanine;

N-[{1-[(2-chlorophenyl)methyl]-2-n-butyl-1H-imidazol-5-yl}methyl]homophenylalanine;

N-[{1-[(2-chlorophenyl)methyl]-2-n-butyl-1H-imidazol-5-yl}ethyl]-α-methylphenylalanine;

N-[{1-[(2-chlorophenyl)methyl]-2-n-butyl-1H-imidazol-5-yl}methyl]-N-methylphenylalanine; or a pharmaceutically acceptable salt thereof.

7. A pharmaceutical composition comprising a compound of claim 1 and a suitable pharmaceutical carrier.

8. A pharmaceutical composition of claim 7 wherein the compound is N-[{1-[(4-carboxyphenyl)methyl]-2-n-butyl-1H-imidazol-5-yl}methyl]phenylalanine.

9. A pharmaceutical composition of claim 7 wherein the compound is N-[{1-[(4-carboxyphenyl)methyl]-2-n-butyl-1H-imidazol-5-yl}methyl]-β-(2-thienyl)alanine.

10. A pharmaceutical composition of claim 7 wherein the compound is N-[{1-[(2-chlorophenyl)methyl]-2 n-butyl-1H-imidazol-5-yl}methyl]-β-(2-thienyl)alanine.

11. A pharmaceutical composition of claim 7 wherein the compound is:

N-[{1-[(2-chlorophenyl)methyl]-2-n-butyl-1H-imidazol-5-yl}methyl]-α-methyl-β-(2-thienyl)-alanine;

N-[{1-[(2-chlorophenyl)methyl]-2-n-butyl-1H-imidazol-5-yl}methyl]phenylalanine;

N-[{1-[(2-chlorophenyl)methyl]-2-thiopropyl-1H-imidazol-5-yl}methyl]phenylalanine;

N-[{1-[(2-chlorophenyl)methyl]-2-thiopropyl-1H-imidazol-5-yl}methyl]-N-butyrylphenylalanine;

N-[2-{1-[(2-chlorophenyl)methyl]-2-n-butyl-1H-imidazol-5-yl}ethyl]phenylalanine;

N-[2-{1-[(2-chlorophenyl)methyl]-2-n-butyl-1H-imidazol-5-yl}ethyl]-β-(2-thienyl)alanine;

N-[2-{1-[(2-chlorophenyl)methyl]-2-n-butyl-1H-imidazol-5-yl}methyl]-β-(2-thienyl)alanine;

N-[{1-[(2-chlorophenyl)methyl]-2-n-butyl-1H-imidazol-5-yl}methyl]-α-ethylphenylalanine;

N-[{1-[(2-chlorophenyl)methyl]-2-n-butyl-1H imidazol-5-yl}methyl]-α-propylphenylalanine;

N-[{1-[(2-chlorophenyl)methyl]-2-n-butyl-1H-imidazol-5-yl}methyl]-N-acetylphenylalanine;

N-[{1-[(2-chlorophenyl)methyl]-2-n-butyl-1H-imidazol-5-yl}methyl]homophenylalanine;

N-[{1-[(2-chlorophenyl)methyl]-2-n-butyl-1H-imidazol-5-yl}ethyl]-α-methylphenylalanine;

N-[{1-[(2-chlorophenyl)methyl]-2-n-butyl-1H-imidazol-5-yl}methyl]-N-methylphenylalanine; or N-[{1-[(2-chlorophenyl)methyl]-2-n-butyl-1H-imidazol-5-yl}methyl]-α-methylphenylalanine.

12. A method of antagonizing angiotensin II receptors in mammals which comprises administering to a subject in need thereof an effective amount of a compound of claim 1.

13. A method of claim 12 wherein the compound is N-[{1-[(4-carboxyphenyl)methyl]-2-n-butyl-1H-imidazol-5-yl}methyl]phenylalanine.

14. A method of claim 12 wherein the compound is N-[1-{[(4-carboxyphenyl)methyl]-2-n-butyl-1H-imidazol-5-yl}methyl]-β-(2-thienyl)alanine.

15. A method of claim 12 wherein the compound is N-[{1-[(2-chlorophenyl)methyl]-2-n-butyl-1H-imidazol-5-yl}methyl]-β-(2(thienyl)alanine.

16. A method of claim 12 wherein the compound is:

N-[{1-[(2-chlorophenyl)methyl]-2-n-butyl-1H-imidazol-5-yl}-methyl]-α-methyl-β-(2-thienyl)alanine;

N-[{1-[(2-chlorophenyl)methyl]-2-n-butyl-1H-imidazol-5-yl}methyl]phenylalanine;

N-[(1-[(2-chlorophenyl)methyl]-2-thiopropyl-1H-imidazol-5-yl}methyl]phenylalanine;

N-[{1-[(2-chlorophenyl)methyl]-2-thiopropyl-1H-imidazol-5-yl}methyl]-N-butyrylphenylalanine;

N-[(2-chlorophenyl)methyl]-2-n-butyl-1H-imidazol-5-yl]ethyl]phenylalanine;

N-[2-{1-[(2-chlorophenyl)methyl]-2-n-butyl-1H-imidazol-5-yl}ethyl]-β-(2-thienyl)alanine;

N-[2-{1-[(2-chlorophenyl)methyl]-2-n-butyl-1H-imidazol-5-yl}methyl]-β-(2-thienyl)alanine;

N-[{1-[(2-chlorophenyl)methyl]-2-n-butyl-1H-imidazol-5-yl}methyl]-α-ethylphenylalanine;

N [{1-[(2-chlorophenyl)methyl]-2-n butyl-1H-imidazol-5 yl}methyl]-α-propylphenylalanine;

N-[{1-[(2-chlorophenyl)methyl]-2-n-butyl-1H-imidazol-5-yl}methyl]-N-acetylphenylalanine;

N-[{1-[(2-chlorophenyl)methyl]-2-n-butyl-1H-imidazol-5-yl}methyl]homophenylalanine;

N-[{1-[(2-chlorophenyl)methyl]2-n-butyl-1H-imidazol-5-yl}methyl]-α-methylphenylalanine;

N-[{1-[(2-chlorophenyl)methyl]-2-n-butyl-1H-imidazol-5-yl}ethyl]-α-methylphenylalanine; or N-[{1-[(2-chlorophenyl)methyl]-2-n-butyl-1H imidazol-5-yl}methyl]-N-methylphenylalanine.

17. A method of producing antihypertensive activity in mammals which comprises administering to a subject in need thereof an effective amount of a compound of claim 1.

18. A method of treating congestive heart failure in mammals which comprises administering to a subject in need thereof an effective amount of a compound of claim 1.

19. A method of treating renal failure in mammals which comprises administering to a subject in need thereof an effective amount of a compound of claim 1.

20. A method of treating glaucoma in mammals which comprises administering to a subject in need thereof an effective amount of a compound of claim 1.

* * * * *

UNITED STATES PATENT AND TRADEMARK OFFICE
CERTIFICATE OF CORRECTION

PATENT NO. : 5,248,689

DATED : September 28, 1993

INVENTOR(S) : Girard, Hill, Weinstock

It is certified that error appears in the above-identified patent and that said Letters Patent is hereby corrected as shown below:

In claim 1, column 27, line 68, replace "$SO_1C_1-C_6 alkyl$" with -- $SO_2C_1-C_6 alkyl$ --.

In claim 1, column 28, lines 29 and 30, replace "NRCOW" with -- $NR^7COW$ --.

In claim 5, column 28, line 58, replace "(2-chloro)" with -- (2-chlorophenyl) --.

In claim 6, column 29, line 2, replace "N-butyrylphenylalanine" with -- phenylalanine --.

In claim 6, column 29, line 3, replace "n-butyl" with -- thiopropyl --.

In claim 6, column 29, line 6, replace "phenyl)alanine" with -- phenylalanine --.

UNITED STATES PATENT AND TRADEMARK OFFICE
CERTIFICATE OF CORRECTION

PATENT NO. : 5,248,689
DATED : September 28, 1993
INVENTOR(S) : Girard, Hill, Weinstock It is certified that error appears in the above-indentified patent and that said Letters Patent is hereby corrected as shown below:

In claim 6, column 29, line 8, replace "methyl" with --ethyl--.

Signed and Sealed this

Twenty-fifth Day of June, 1996

Attest:

BRUCE LEHMAN

Attesting Officer    Commissioner of Patents and Trademarks